United States Patent [19]

Cook

[11] Patent Number: 5,073,299

[45] Date of Patent: Dec. 17, 1991

[54] TELOMERIC COMPOUND

[75] Inventor: Barry Cook, Manchester, England

[73] Assignee: Ciba-Geigy Corporation, Ardsley, N.Y.

[21] Appl. No.: 409,225

[22] Filed: Sep. 19, 1989

[30] Foreign Application Priority Data

Sep. 21, 1988 [GB] United Kingdom ............... 8822144

[51] Int. Cl.$^5$ .............................................. C23F 11/10
[52] U.S. Cl. ................................. 252/389.23; 558/104;
558/180; 560/180; 560/190; 560/145; 560/130;
422/15; 422/17; 210/699
[58] Field of Search ................ 558/104, 180; 560/180,
560/190, 145, 130; 252/389.23, 15, 17, 699;
422/15, 17; 210/699

[56] References Cited

U.S. PATENT DOCUMENTS

| 2,971,019 | 2/1961 | Ladd et al. ........................... 558/180 |
| 3,048,613 | 8/1962 | Ladd et al. ........................... 558/180 |
| 4,046,707 | 9/1977 | Smith et al. ...................... 252/181 X |
| 4,105,551 | 8/1978 | Smith et al. ........................... 210/699 |
| 4,127,483 | 11/1978 | Smith et al. ........................... 210/699 |
| 4,159,946 | 7/1979 | Smith et al. ........................... 210/699 |

FOREIGN PATENT DOCUMENTS 509034 1/1955 Canada .
660169 10/1951 United Kingdom .
695782 8/1953 United Kingdom .

OTHER PUBLICATIONS

B. E. Ivanor et al., Z. Obsch. Khim. 49, 1768 (1979).
Japanese 59-98150 (Patent Abst.).
Japanese 60-11566 (Patent Abst.).

Primary Examiner—Deborah L. Kyle
Assistant Examiner—Valerie Fee
Attorney, Agent, or Firm—Luther A. R. Hall

[57] ABSTRACT

Compounds having the formula I:

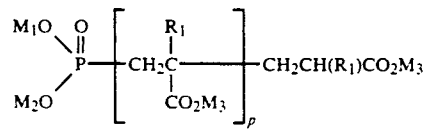

wherein $M_1$, $M_2$, $M_3$, independently, are hydrogen, $C_1$-$C_4$ alkkyl, phenyl, a monovalent or an equivalent of a polyvalent metal atom, ammonium or a substituted ammonium ion; $R_1$ is $C_1$-$C_4$ alkyl substituted by one or more hydroxy or carboxyl groups; and p is an integer.

The new compounds are useful in the treatment of aqueous systems, in particular to inhibit scale deposition from aqueous systems.

12 Claims, No Drawings

TELOMERIC COMPOUND

The present invention relates to new compounds, to their production and to their use in the treatment of aqueous systems, in particular to inhibit scale deposition from the aqueous system and/or to prevent fouling of the aqueous system and/or to inhibit corrosion of metals in contact with the aqueous system.

In our British Patent Specification No. 1458235, there is described and claimed a method of inhibiting the precipitation of the scale forming salts of clacium, magnesium, barium and strontium from aqueous systems over a wide temperature range, comprising adding to the aqueous system a minor proportion of a product comprising a telomeric compound of the formula:

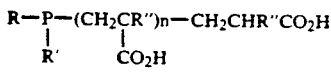

and salts thereof, wherein R'' is hydrogen or a methyl or ethyl residue, R is hydrogen, a straight- or branched alkyl residue, having from 1 to 18 carbon atoms, a cycloalkyl residue having from 5 to 12 carbon atoms, an aryl residue, an aralkyl residue, a residue of formula:

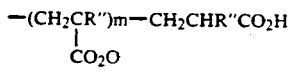

wherein R'' has its previous significance and the sum n+m is an integer of at the most 100, or a residue —OX wherein X is hydrogen or a straight- or branched alkyl residue having from 1 to 4 carbon atoms and R' is a residue —OX wherein X has its previous significance.

We have now found that certain new compounds which, unexpectedly, have superior activity in the inhibition of scale deposition from aqueous systems and additionally have superior activity in the control of corrosion of metals in contact with aqueous systems.

Accordingly, the present invention provides compounds having the formula I:

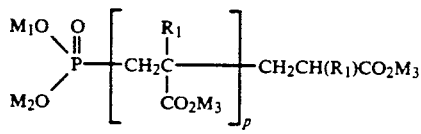

wherein $M_1$, $M_2$, $M_3$, independently, are hydrogen, $C_1$-$C_4$alkyl, phenyl, a monovalent or an equivalent of a polyvalent metal atom, ammonium or a substituted ammonium ion; $R_1$ is $C_1$-$C_4$alkyl substituted by one or more hydroxy or carboxyl groups and p is an integer.

E.g. one or more of preferably all three of $M_1$, $M_2$ and $M_3$ are hydrogen, a monovalent or an equivalent of a polyvalent metal atom, ammonium or a substituted ammonium ion.

p is an integer ranging e.g. from 1 to 1000, preferably ranging from 1 to 99 and most preferred ranging from 1 to 20.

When one or more of $M_1$, $M_2$ and $M_3$ is a metal atom, they may be e.g. an alkali metal atom or an alkaline earth metal. Typical alkali metal atoms are e.g. sodium and potassium atoms and typical alkaline earth metal atoms are e.g. calcium, barium and strontium atoms. Substituted ammonium ions include e.g. trimethylammonium, triethylammonium, bis(2-hydroxyethyl) ammonium, tris(2-hydroxyethyl) ammonium and bis(2-hydroxyethyl)-(2-hydroxy-3-p-nonylphenoxy propyl ammonium ions.

When one or more of $M_1$, $M_2$ and $M_3$ is a $C_1$-$C_4$alkyl residue, they may be e.g. methyl, ethyl, n-propyl, i-propyl, n-butyl, i-butyl or tert-butyl.

When $R_1$ is $C_1$-$C_4$alkyl substituted by one or more hydroxy or carboxyl groups, it may be e.g. hydroxymethyl, 2-hydroxypropyl, carboxymethyl, carboethoxylmethyl, 2-carboxyethyl, 2-carboethoxyethyl, 1,2-dicarboxyethyl, 1,2-dicarbomethoxyethyl, 2,4-dicarboxybutyl or 2,4-di-carbomethoxybutyl. Preferred for $R_1$ are carboxymethyl, carboxyethyl and 1,2-dicarboxyethyl.

The new compounds of formula I may be produced by reacting p+1 moles of a compound of formula II:

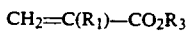

and one mole of a compound having the formula III:

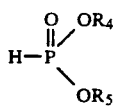

wherein $R_1$ has its previous significance, and $R_3$, $R_4$ and $R_5$, independently, are hydrogen, $C_1$-$C_4$alkyl, phenyl, a monovalent or an equivalent of a polyvalent metal ion, ammonium or a substituted ammonium ion, or $R_4$ and $R_5$ may be linked by a —$CH_2CH_2$— residue to form a cyclic ring structure.

Typical metal ions $R_3$, $R_4$ and $R_5$, and optionally substituted ammonium ions $R_3$, $R_4$ and $R_5$, respectively, are those previously indicated under the definition of $M_1$, $M_2$, and $M_3$.

The reaction may be effected, in the presence or absence of a solvent, and in the presence of a free radical initiator e.g. organic peroxides such as di-tert.butyl peroxide, benzoyl peroxide, bisazoisobutyronitrile, hydrogen peroxide, sodium peroxide and sodium perborate. If a solvent is used, this may be e.g. water, an aromatic hydrocarbon such as toluene; dioxan; a ketone such as 2-butanone; or an alcohol e.g. isopropanol; each optionally in admixture with water.

The products of the process according to the present invention are water-soluble. When, a reactant of formula II or III is used which contains a group $R_3$, $R_4$ or $R_5$ which is $C_1$-$C_4$alkyl or phenyl, such groups may be partially or fully hydrolysed to subsequently produce a compound of formula I containing the corresponding groups $M_1$, $M_2$ and $M_3$, wherein $M_1$, $M_2$ and $M_3$ have their previous significance. Such compounds of formula I are produced by the said hydrolysis followed by substitution of some or all of the acidic hydrogen atoms so obtained, by cations of the salt-forming bases, hereinbefore defined.

Reactants of formula II include itaconic acid, dimethyl itaconate, but-1-en-2,4-dicarboxylic acid, diethyl but-1-ene-2,4-dicarboxylate, hex-1-en-2,4,6-tricarboxylic acid, triethyl-hex-1-en-2,4,6-tricarboxylate, but-1-en-2,3,4-tricarboxylic acid, trimethyl but-1-en-1,3,4-tricarboxylate, 2-hydroxymethyl acrylic acid and 2-hydroxyethyl acrylic acid.

Reactants of formula III include phosphorous acid, di-ethyl phosphite, di-methyl phosphite, di-butyl phosphite, di-phenyl phosphite, ethylene phosphite and sodium hydrogen phosphite.

The compounds of formula I are effective in inhibiting deposition of scale and precipitation of salts from aqueous solutions. The compounds are particularly effective in combatting scale-forming salts derived from calcium, magnesium, barium, or strontium cations and anions such as sulphate, carbonate, hydroxide, phosphate or silicate. The compounds of formula I are especially effective in inhibiting deposition of calcium sulphate, magnesium hydroxide, calcium phosphate and calcium carbonate scale.

The compounds of formula I also function as dispersing agents and/or antifoulants towards common deposits found in water used in commercial plants e.g. industrial boilers, cooling water systems, gas scrubbing plants and aqueous slurries found in china clay operations. Examples of such deposits are iron oxides, calcium and magnesium deposits e.g. their carbonates, sulphates, oxalates and phosphates, and silt, alumina, silicates and clays.

The compounds of formula I also provide excellent inhibition against corrosion of metals, especially ferrous metals, in contact with water.

Still further, the compounds of formula I are useful for inhibiting the thick velvety coating (sealing smut) which can be deposited over the surface of aluminium during the sealing of anodically produced oxide layers on the aluminum, using hot or boiling water.

The products of the process of the present invention are obtained as solutions. For the purpose of isolation they may be subjected to partial or complete evaporation under reduced pressure. The reaction products may be used as the telomeric products in the method of the invention as described hereinafter.

Salt forms of the compounds of formula I in which some or all of the acidic hydrogens in the compounds of formula I have been replaced by the cations derived from the salt forming bases hereinbefore defined, may be prepared by mixing an aqueous or alcoholic solution of the compound of formula I with an aqueous or alcoholic solution of the compound of formula I with an aqueous or alcoholic solution containing an amount of the requisite base in excess of, equal to or less than the stoichiometric requirement. The solvent may then be removed by evaporation. In many of the water-containing systems where inhibitors of this invention would prove useful, the water is sufficiently alkaline to effect neutralisation and only the product of the invention need be added.

The present invention also provides a method of treating an aqueous system comprising adding to the system a telomer compound of formula I.

In practice, the amount of the compound of formula I used to treat the aqueous system may vary according to the protective function which the compound is required to perform.

For example, for corrosion-inhibiting protective treatments, optionally with simultaneous scale-inhibiting treatments, the amount of the compound of formula I added to the aqueous system may range from 0.1 to 50,000 ppm (0.00001 to 5% by weight), preferably from 1 to 500 ppm (0.0001 to 0.05% by weight), based on the weight of the aqueous system.

For solely anti-scale treatments, the amount of the compound of formula I added is conveniently from 1 to 200, preferably 1 to 30 ppm, based on the aqueous system. For most relatively dilute aqueous dispersions to be treated, the amount of compound of formula I to be added as dispersant/antifoulant is conveniently from 1 to 200 ppm, preferably 2 to 20 ppm by weight. Aqueous slurries to be treated, however, may require much higher levels of compound of formula I e.g. from 0.1 to 5% by weight on total solids—which can be as high as 70% by weight of the total aqueous system.

When used to inhibit the deposition of scale and the precipitation of salts from aqueous solutions, the compounds of formula I, or salts thereof, are particularly effective in inhibiting deposition of scale-forming salts derived from calcium, magnesium, barium or strontium cations, and anions such as sulphate, carbonate, hydroxide, phosphate and silicate.

With respect to aqueous system which may be treated according to the present invention, of particular interest with respect to combined corrosion inhibition and antiscale treatments are cooling water system, steam generating systems, sea-water evaporators, reverse osmosis equipment, paper manufacturing equipment, sugar evaporator equipment, soil irrigation systems, hydrostatic cookers, gas scrubbing systems, closed circuit heating systems, aqueous-based refrigeration systems and down-well systems; for corrosion inhibition treatments alone, aqueous systems of particular interest include aqueous machining fluid formulations (e.g. for use in boring, milling, reaming, broaching, drawings, spinning, turning, cutting, sawing, grinding, and thread-cutting operations or in non-cutting shaping in drawing or rolling operations) aqueous souring systems, engine coolants including aqueous glycol antifreeze systems, water/glycol hydraulic fluids; and aqueous based polymer surface-coating systems/or solvent-based polymer systems, e.g. those containing tetrahydrofuran, ketones or alkoxyalkanols.

The inhibitor compound of formula I used according to the invention may be used alone, or in conjunction with other compounds known to be useful in the treatment of aqueous systems.

In the treatment of systems which are completely aqueous, such as cooling water systems, air-conditioning systems, steam-generating systems, sea-water evaporator systems, hydrostatic cookers, and closed circuit heating or refrigerant systems, further corrosion inhibitors may be used such as, for example, water soluble zinc salts; phosphates; polyphosphates; phosphonic acids and their salts, for example, hydroxyethyl diphosphonic acid (HEDP), nitrilotris methylene phosphonic acid and methylamino dimethylene phosphonocarboxylic acids and their salts, for example, those described in German Offenlegungsschrift 2632774, hydroxyphosphonoacetic acid, 2-phosphonobutane-1,2,4-tri-carboxylic acid and those disclosed in GB 1572406; nitrates, for example, sodium nitrate; nitrites, e.g. sodium nitrite; molybdates, e.g. sodium molybdate, tungstates; silicates, e.g. sodium silicate; benzotriazole, bis-benzotriazole or copper deactivating benzotriazole or tolutriazole derivatives or their Mannich base derivatives; mercaptobenzotriazole; N-acyl sarcosines; N-acylimino diacetic acids; ehtanolamines; fatty amines; and polycarboxylic acids, for example, polymaleic acid and polyacrylic acid, as well as their respective alkali metal salts, copolymers of maleic anhydride, e.g. copolymers o maleic anhydride and sulfonated styrene, copolymers of acrylic acid, e.g. copolymers of acrylic acid an hydroxyalkylated acrylic acid, and substituted derivatives of polymaleic and polyacrylic acids and their copolymers. Moreover, in such completely aqueous systems, the inhibitor used according to the invention may be used in conjunction with further dispersing and/or threshold agents, e.g. polymerised acrylic acid (or its salts), phophino-polycarboxylic acids (as described and claimed in British Patent 1458235), the cotelomeric compounds described in European Patent Application No. 0150706, hydrolysed polyacrylonitrile, polymerised meth-acrylic acid and its salts, polyacrylamide and copolymers thereof from acrylic and methacrylic acids, lignin sulphonic acid and its salts, tannin, naphthalene sulphonic acid/formaldehyde condensation products, starch and its derivatives, cellulose, acrylic acid/lower alkyl hydroxy-acrylate copolymers, e.g. those described in U.S. Pat. No. 4,029,577, styrene/maleic anhydride copolymers and sulfonated styrene homopolymers, e.g. those described in U.S. Pat. No. 4,374,733 and combinations thereof. Specific threshold agents, such as for example, 2-phosphono-butane-1,2,4-tri-carboxylic acid (PBSAM), hydroxyethyl diphosphonic acid (HEDP), hydrolysed polymaleic anhydride and its salts, alkyl phosphonic acids, hydroxyphosphonoacetic acid, 1-aminoalkyl-1,1-diphosphonic acids and their salts, and alkali metal polyphosphates, may also be used.

Particularly interesting additive packages are those comprising compounds of formula I with one or more of polymaleic acid or polyacrylic acid or their copolymers, or substituted copolymers, hydroxyphosphonoacetic acid, HEDP, PBSAM, triazoles such as tolutriazole, molybdates and nitrites.

Precipitating agents such as alkali metal orthophosphates, carbonates; oxygen scavengers such as alkali metal sulphites and hydrazines; sequestering agents such as nitrilotriacetic acid and its salts; antifoaming agents such as silicones, e.g. polydimethylsiloxanes, distearylsebacamide, distearyl adipamide and related products derived from ethylene oxide and/or propylene oxide condensation, in addition to fatty alcohols, such as capryl alcohols and their ethylene oxide condenstes; and biocides, e.g. amines, quaternary ammonium compounds, chlorophenols, sulphur-containing compounds such as sulphones, methylene bis thiocyanates and carbamates, isothiazolones, brominated propionamides, triazines, phosphonium compounds, chlorine and chlorine-release agents and organometallic compounds such as tributyl tin oxide, may be used.

If the system to be treated by the method of the invention is not completely aqueous, e.g. an aqueous machining fluid formulation, it may be e.g. a water dilutable cutting or grinding fluid.

The aqueous maching fluid formulations of the invention may be, e.g. metal working formulations. By "metal working", we mean reaming, broaching, drawing, spinning, cutting, grinding, boring, milling, turning, sawing, non-cutting shaping or rolling. Examples of water-dilutable cutting or grinding fluids into which the corrosion inhibiting combination may be incorporated include:

a) aqueous concentrates of one or more corrosion inhibitors, and optionally one or more anti-wear additives, used at dilutions of 1:50 to 1:100, which are usually employed as grinding fluids;

b) polyglycols containing biocides, corrosion inhibitors and anti-wear additives which are used at dilutions of 1:20 to 1:40 for cutting operations and 1:60 to 1:80 for grinding;

c) semi-synthetic cutting fluids similar to (b) but containing in addition 10 to 25% oil with sufficient emulsifier to render the water diluted product translucent;

d) an emulsifiable mineral oil concentrate containing, for example, emulsifiers, corrosion inhibitors, extreme pressure/anti-wear additives, biocides, antifoaming agents, coupling agents etc; they are generally diluted from 1:10 to 1:50 with water to a white opaque emulsion;

e) a product similar to (d) containing less oil and more emulsifier which on dilution to the range 1:50 to 1:100 gives a translucent emulsion for cutting or grinding operations.

For those partly-aqueous systems in which the aqueous system component is an aqueous machining fluid formulation the inhibitor of formula I used according to the invention may be used singly, or in admixture with other additives, e.g. known further corrosion inhibitors and/or extreme-pressure additives.

Examples of other corrosion inhibitors which may be used in these aqueous systems, in addition to the inhibitor composition used according to the invention, include the following groups:

a) Organic acids, their esters or ammonium, amine, alkanol-amine and metal salts, for example, benzoic acid, p-tert-butyl benzoic acid, disodium sebacate, triethanolamine laurate, isononanoic acid, triethanolamine salt of (p-toluene sulphonamido caproic acid), triethanolamine salt of benzene sulphonamido caproic acid, triethanolamine salts of 5-ketocarboxylic acid derivatives as described in European Patent No. 41927, sodium N lauroyl sarcosinate or nonyl phenoxy acetic acid;

b) Nitrogen-containing materials such as the following types: fatty acid alkanolamides; imidazolines, for example, 1-hydroxy-ethyl-2-oleyl-imidazolines, oxazolines; triazoles for example, benzotriazoles; or their Mannich base derivatives, triethanolamines; fatty amines; inorganic salts, for example, sodium nitrate; and the carboxy-triazine compounds described in European Patent Application No. 46139;

c) Phosphorus containing materials such as the following types: amine phosphates, phosphonic acids or inorganic salts, for example, sodium dihydrogen phosphate or zinc phosphate;

d) Sulphur containing compounds such as the following types: sodium, calcium or barium petroleum sulphonates, or heterocyclics, for example, sodium mercaptobenzothiazole.

Nitrogen containing materials, particularly triethanolamine, are preferred.

Examples of extreme pressure additives which may be present in the systems treated according to the present invention include sulphur and/or phosphorus and/or halogen containing materials, for instance, sulphurised sperm oil, sulphurised fats, tritolyl phosphate, chlorinated paraffins or ethoxylated phosphate esters.

When triethanolamine is present in the aqueous systems treated according to the present invention, it is preferably present in an amount such that the ratio of inhibitor composition to triethanolamine is from 2:1 to 1:20.

The partly-aqueous systems treated by the method of the present invention may also be aqueous surface-coating compositions, e.g. emulsion paints and aqueous powder coatings for metallic substrates.

The aqeous surface-coating composition may be, e.g. a paint such as a styrene-acrylic copolymer emulsion paint, a resin, latex, or other aqueous based polymer surface-coating systems, to coat a metal substrate. The inhibitor composition used according to the invention may be employed to prevent flash rusting of the metal substrate during application of the surface coating and to prevent subsequent corrosion during use of the coated metal.

In aqueous surface-coating compositions treated by the method of the invention the inhibitor composition may be used singly, or in admixture with other additives, e.g. known corrosion inhibitors, biocides, emulsifiers and/or pigments.

The further known corrosion inhibitors which may be used are, e.g. those of classes a), b), c) and d) hereinbefore defined.

Examples of biocides which may be used in these aqueous systems, in addition to the compound of formula I, include the following:

Phenols, and alkyl- and halogenated phenols, for example, pentachlorophenol, o-phenylphenol, o-phenoxyphenol and chlorinated o-phenoxyphenol, and salicylanilides, diamines, triazines and organometallic compounds such as organomercury compounds and organotin compounds.

Examples of emulsifiers for aqueous surface coatings include alkyl sulfates, alkyl sulfonates, ether-alcohol sulphonates, di-n-alkyl sulphosumates and polyoxyethylen nonylphenyl ethers.

Examples of pigments which may be used in these aqueous systems, in addition to the compound of formula I, include titanium dioxide, zinc chromate, iron oxide and organic pigments such as the phthalocyanines.

As already indicated compounds of formula I also function as dispersing agents and/or antifoulants towards common deposits, e.g. iron oxides and/or iron salts, calcium and magnesium deposits, e.g. their carbonates, sulphates, oxalates and phosphates, and silt, alumina, silicates and clays found in such waters.

In particular, the method of the present invention may be applied to disperse deposits in an aqueous system containing 5 to 1500 ppm by weight of calcium ion as well as suspended solids. This aspect of the present invention finds particular use in the china clay industry in which it is important to obtain slurries which will not appreciably separate out during transportation from the clay pits to the user. At high concentrations of suspended solids in these slurries, the compounds of formula I have been found to disperse china clay and to be of value as "in-process" dispersants and as grinding aids.

The following Examples further illustrate the present invention. All parts and percentages are by weight, unless stated otherwise.

EXAMPLE 1

To 12.1 parts by weight of di-ethylphosphite are added, separately, 70 parts by weight of diethyl but-1-en-2,4-dicarboxylate and 5.75 parts by weight of di-tert-butylperoxide, dropwise, over 3 hours, with stirring at 140° C. The temperature is maintained at 140° C. for a further 2 hours after the additions are complete. Unreacted di-ethyl-phosphite is removed by distillation under reduced pressure up to 200°/130 Pa and the residual liquid is suspended in 400 parts by weight of concentrated hydrochloric acid, and the mixture heated under reflux conditions for 18 hours.

The resulting solution is evaporated to dryness under reduced pressure at 100° C./1600 Pa to give 53 parts by weight of a solid polymer having a molecular weight of 1430.

The absence of phosphorous acid and the presence of the phosphonic acid telogen is proven be $^{31}$P nmr analysis (multiple signals at 28 ppm).

EXAMPLE 2

Following the procedure described in Example 1, from 23 parts by weight of diethylphosphite, 52.7 parts by weight of di-methyl itaconate ad 5.3 parts by weight of di-tert-butyl-peroxide there are obtained 44.5 parts by weight of a polymer having a molecular weight of 590 and a $^{31}$P multiple spectrum around 25–30 ppm.

EXAMPLE 3

Calcium carbonate (cooling water) threshold test

Test Conditions

| Test temperature | 70° C. |
|---|---|
| Test duration | 30 minutes |
| Aeration rate | 500 cc/min (per 100 ml) |
| Calcium | 150 ppm as $Ca^{2+}$ |
| Magnesium | 45 ppm as $Mg^{2+}$ |
| Carbonate | 51 ppm as $CO_3^{2-}$ |
| Bicarbonate | 269 ppm as $^-HCO_3$ |
| Test additive | 1 ppm |

The test is designed to assess the ability of an additive to inhibit the precipitation of $CaCO_3$. The water composition simulates cooling water and the high temperature represents the conditions which exist close to a heat exchanger. Air bubbling is used to increase the severity of the test conditions.

A volume of solution containing sodium carbonate and sodium bicarbonate is mixed with an equal volume of a solution containing calcium chloride and magnesium chloride which already contains the test additive. The resulting test solution, through which air is bubbled at a contant rate, is stored at 70° C. for 30 minutes. After this time, the solution is filtered and the calcium remaining in the filtrate is determined by EDTA titration.

Each test is carried out in duplicate, and the first test is a standard test which determines the actual $Ca^{2+}$ concentration in the test.

$$\% \text{ CaCO}_3 \text{ inhibition} = \frac{\text{titre of test} - \text{titre of blank}}{\text{titre of standard} - \text{titre of blank}} \times 100$$

The standard and blank titres are usually 15–16 ml and 5–6 ml, respectively.

The product of Example 1, at 1 ppm level of addition, gave a % $CaCO_3$ inhibition of 63.

What is claimed is:

1. A compound having the formula I:

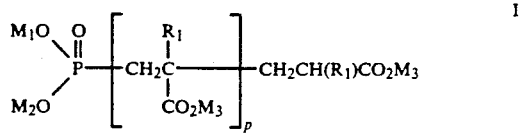

wherein $M_1$, $M_2$, $M_3$, independently, are hydrogen, $C_1$–$C_4$alkyl, phenyl, a monovalent or an equivalent of a polyvalent metal atom, ammonium or a substituted ammonium ion; $R_1$ is $C_1$–$C_4$alkyl substituted by one or more hydroxy or carboxyl groups and p is an integer.

2. A compound according to claim 1 wherein p is an integer within the range of from 1 to 99.

3. A compound according to claim 1 wherein p is an integer within the range from 1 to 20.

4. A compound according to claim 1 wherein all three of $M_1$, $M_2$ and $M_3$ are hydrogen, a monovalent or an equivalent of a polyvalent metal atom, ammonium or a substituted ammonium ion.

5. Method of treating an aqueous system comprising adding to the system a compound of formula I as defined in claim 1.

6. Method according to claim 5 wherein the system is treated to provide a corrosion-inhibiting treatment, or a corrosion-inhibiting with simultaneous scale-inhibiting treatments, and the compound of formula I is added in amount of from 0.1 to 50,000 ppm by weight, based on the weight of the aqueous system.

7. Method according to claim 6 wherein the compound of formula I is added in amount of 1 to 500 ppm by weight, based on the aqueous system.

8. Method according to claim 5 wherein the system is treated to provide solely an anti-scale treatment and the compound of formula I is added in amount of 1 to 200 ppm by weight, based on the aqueous system.

9. Method according to claim 8 wherein the compound of formula I is added in amount of 1 to 30 ppm by weight, based on the aqueous system.

10. Method according to claim 5 wherein the system is treated to provide a dispersant/anti-foulant treatment and the amount of compound of formula I added is from 1 to 200 ppm by weight based on the aqueous system.

11. Method according to claim 10 wherein the compound of formula I is added in amount of 1 to 30 ppm by weight, based on the aqueous system.

12. Method according to claim 5 wherein the compound of formula I is used in conjunction with one or more of polymaleic or polyacrylic acid or their copolymers, or substituted copolymers; hydroxyphosphonoacetic acid, HEDP; PBSAM; triazoles such as tolutriazole; molybdates; and nitrites.

* * * * *